(12) United States Patent
Heggelund et al.

(10) Patent No.: US 8,048,853 B2
(45) Date of Patent: Nov. 1, 2011

(54) PROCESS FOR PREPARING PHARMACEUTICAL COMPOUND AND INTERMEDIATES THEREOF

(75) Inventors: Audun Heggelund, Oslo (NO); Ole Heine Kvernenes, Oslo (NO); Vidar Bjørnstad, Sørumsand (NO)

(73) Assignee: Xellia Pharmaceuticals APS, Copenhagen (DK)

( * ) Notice: Subject to any disclaimer, the term of this patent is extended or adjusted under 35 U.S.C. 154(b) by 688 days.

(21) Appl. No.: 12/138,488

(22) Filed: Jun. 13, 2008

(65) Prior Publication Data

US 2009/0312541 A1    Dec. 17, 2009

(51) Int. Cl.
*A61K 38/12* (2006.01)
*C07K 1/00* (2006.01)
(52) U.S. Cl. ......... 514/3.3; 514/21.1; 530/317; 530/333
(58) Field of Classification Search .................. None
See application file for complete search history.

(56) References Cited

U.S. PATENT DOCUMENTS

| | | |
|---|---|---|
| 5,336,756 A | 8/1994 | Schwartz et al. |
| 5,348,940 A | 9/1994 | Balkovec |
| 5,378,804 A | 1/1995 | Balkovec |
| 5,552,521 A | 9/1996 | Belyk et al. |
| 5,668,105 A | 9/1997 | Balcovec et al. |
| 5,792,746 A | 8/1998 | Balcovec et al. |
| 5,936,062 A | 8/1999 | Leonard et al. |
| 5,939,384 A | 8/1999 | Hammond et al. |
| 5,952,300 A | 9/1999 | Nerurkar |
| 7,214,768 B2 | 5/2007 | Belyk |

FOREIGN PATENT DOCUMENTS

| | | |
|---|---|---|
| EP | 535967 | 1/1992 |
| WO | WO 94/21677 | 9/1994 |
| WO | WO 96/08266 | 3/1996 |
| WO | WO 96/24613 | 8/1996 |
| WO | WO 97/39763 | 10/1997 |
| WO | WO 97/47645 | 12/1997 |
| WO | WO 01/07468 | 2/2001 |
| WO | 2007/027141 | 5/2007 |
| WO | WO 2007/057141 | 5/2007 |

OTHER PUBLICATIONS

Vippagunta, et al. "Crystalline solids," Adv. Drug Delivery Rev., 2001,48, 3-26.*
Byrn et al. (Solid State Chemistry of Drugs, 2 Ed. 1999 "Hydrates and Solvates" pp. 233-247.*
Leonard, et al., "Synthesis of the Antifungal β 1,3 glucan Synthase Inhibitor CANCIDAS from Pneumocandin B9", JOC 2007, 72 pp. 2335-2343.
Bansi Lal, et al., "Semisynthesis Modifications of Hemiaminal Function at Ornithine Unit of Mulundocandin, Towards Chemical Stbility and Anifungal Activity", Biorganic & Medical Chemistry 11 (2003) 5189-5198.
EPO Office Action dated May 24, 2011.

* cited by examiner

*Primary Examiner* — Christina Bradley
(74) *Attorney, Agent, or Firm* — Christian D. Abel

(57) ABSTRACT

The present invention relates to novel intermediates of formula VII, (VII)

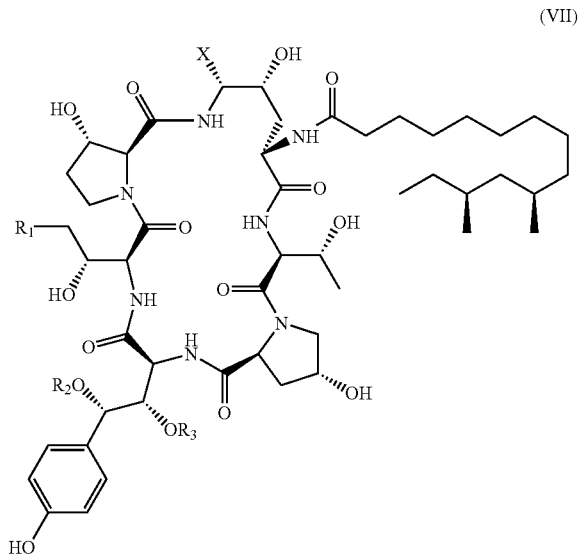

or an acid addition salt or a solvate thereof, wherein $R_1$ is $-(CO)NH_2$, $-CH_2NH_2$ or $-CN$;
$R_2=R_3=H$ or $R_2$ and $R_3$ together form a cyclic boronate or borate ester;
X is a helping group selected from the group consisting of i) a five or six membered heterocyclic aromatic ring and derivatives thereof comprising at least one N-atom being a part of an imine-group, wherein said N-atom forms the point of connection to the cyclohexapeptide ring, and ii) tetrazolyl and derivatives thereof for which a nitrogen atom forms the point of connection to the cyclohexapeptide ring, and a process for the preparation of caspofungin utilizing said intermediates.

11 Claims, No Drawings

PROCESS FOR PREPARING PHARMACEUTICAL COMPOUND AND INTERMEDIATES THEREOF

FIELD OF THE INVENTION

The present invention relates to an improved process for the preparation of caspofungin represented by formula I:

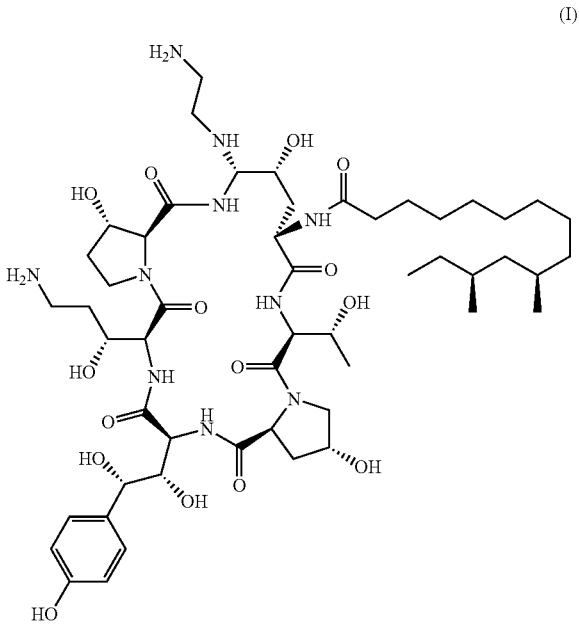

(I)

BACKGROUND

Caspofungin is the first of a new class of semi-synthetic antifungal agents belonging to the class of echinocandins. The drug is prepared by synthetic derivatisation of pneumocandin $B_0$ which is obtained by fermentation of the fungus *Glarea lozoyensis*. Caspofungin inhibits the biosynthesis of β-(1,3)-D-glucan, an integral component of the fungal cell wall, and it is indicated for the treatment of invasive aspergillosis in patients who are refractory to or intolerant of other therapies, as well as empirical therapy for presumed fungal infections in febrile, neutropenic patients. Caspofungin is marketed as its diacetate salt by Merck & Co., under the trade name Cancidas®.

Caspofungin as a compound is claimed in the U.S. Pat. No. 5,378,804 issued to Merck & Co. The drug was prepared in a lengthy synthetic sequence in 0.7% overall yield from pneumocandin $B_0$. The first two synthetic steps were the subject of the patent application EP 0 535 967 A2. Reduction of the primary amide was effected in two steps, i.e. dehydration with cyanuric chloride affording an intermediate nitrite which was reduced with sodium borohydride in the presence of cobalt (II) chloride. The aminal side-chain was introduced via substitution of 2-aminoethanethiol for the hemiaminal hydroxy function, oxidation to the sulfone, followed by substitution with 1,2-diaminoethane.

The pneumocandin $B_0$ reduction product, compound of formula III in Scheme 1, is claimed as a compound in the U.S. Pat. No. 5,939,384.

Journet and coworkers describe an improved two-step reduction of the primary amide in a close echinocandin analogue (Journet et al., *J. Org. Chem.* 1999, 64, 2411-2417). When the cyanuric chloride dehydration was performed at −30° C. with careful control of the water content a very efficient reaction was obtained. The resulting nitrite function was later reduced under catalytic hydrogenation conditions in high yield.

Reduction of the primary amide with borane complexes in one step directly to the corresponding amine is disclosed in U.S. Pat. No. 5,552,521. When pneumocandin $B_0$ was treated with an excess of borane-dimethyl sulfide complex in dry THF at 0° C. the reduction product was obtained in 43% yield. The process was improved further when 2-aminoethanethiol was replaced with thiophenol. One reaction step is omitted as the thiophenol group may be substituted with 1,2-diaminoethane directly without prior oxidation of the sulfide to the sulfone. However, thiophenol is highly malodorous and quite toxic.

The use of boronate ester protection in the synthesis of caspofungin is described in U.S. Pat. No. 5,936,062. Prior to borane reduction of the primary amide, the two vicinal diol systems are protected as the phenylboronate esters. Acidic work-up of the reaction mixture then releases reduced pneumocandin $B_0$ in 61% yield. The patent claims the bis(phenylboronate) derivative of pneumocandin $B_0$.

When pneumocandin $B_0$ is reacted with phenylboronic acid prior to treatment with thiophenol under acid catalysis, certain process impurities may be minimised, cf. U.S. Pat. No. 7,214,768. Epimerisation of the benzylic position, as well as substitution of the benzylic hydroxy function, is suppressed when the benzylic alcohol is derivatised as a boronate ester.

Furthermore, in WO 2007/057141, yet another method for synthesising caspofungin is disclosed. The process relies on the two-step reduction of the primary amide to the amine via the corresponding nitrite and includes new intermediates.

Leonard and coworkers at Merck Research Laboratories provide a detailed description of the development of the caspofungin synthesis, and the presented process is said to be the actual process of manufacture, Leonard et al., *J. Org. Chem.* 2007, 72, 2335-2343. The phenylboronate ester protection is included in the reduction of the primary amide, as well as during the insertion of thiophenol under acid catalysis. The overall yield of caspofungin from pneumocandin $B_0$ is reported to be 45%. The process consists of three chemical reaction steps and two chromatographic purifications.

As substitution of the hemiaminal hydroxy function directly with 1,2-diaminoethane has been found difficult (Leonard et al.), a two-step sequence has been necessary in the introduction of the ethylenediamine side-chain. According to the prevailing method disclosed in the prior art, sulphur nucleophiles such as thiophenol have been used as helping groups since they are readily substituted for the hemiaminal hydroxy function and may be expelled by a second nucleophile (i.e. 1,2-diaminoethane) directly or after oxidation. In particular, thiophenol has been successful as a helping group in the caspofungin synthesis. However, thiophenol is highly malodorous and toxic, and using it on production scale demands special equipment. Thus, a method not being dependent on the use of thiophenol is favourable both from an economical and environmental point of view.

As the prevailing methods of production of caspofungin involve many steps of synthesis and purification, and a substantial amount of material is lost during the process, there is still a need for an improved process of production of caspofungin. Furthermore, the most efficient processes available rely on the use of highly malodorous and toxic thiophenol as a helping group.

SUMMARY OF THE INVENTION

The present inventors have found that caspofungin may be prepared using a novel intermediate of formula VII as shown below rendering it possible to avoid the use of thiols, such as thiophenol for the introduction of a suitable helping group.

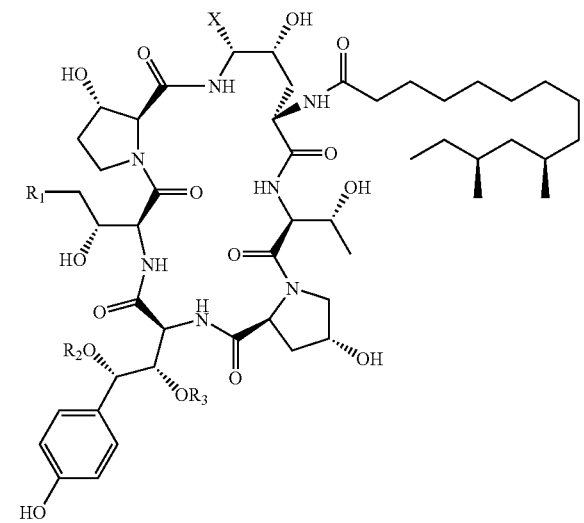

(VII)

or an acid addition salt or a solvate thereof, wherein $R_1$ is —(CO)NH$_2$, —(CO)NH$_2$, or —CH$_2$NH$_2$ or —CN;
$R_2=R_3=H$ or $R_2$ and $R_3$ together form a cyclic boronate or borate ester;
X is a helping group selected from the group consisting of i) a five or six membered heterocyclic aromatic ring and derivatives thereof comprising at least one N-atom being a part of an imine-group, wherein said N-atom forms the point of connection to the cyclohexapeptide ring, and ii) tetrazolyl and derivatives thereof for which a nitrogen atom forms the point of connection to the cyclohexapeptide ring.

According to one aspect of the invention the pneumocandin $B_0$ reduction product of formula III is reacted with a reagent for the introduction of a helping group X, providing an intermediate IV after substitution of the hemiaminal hydroxy function, cf. Scheme 1.

Scheme 1

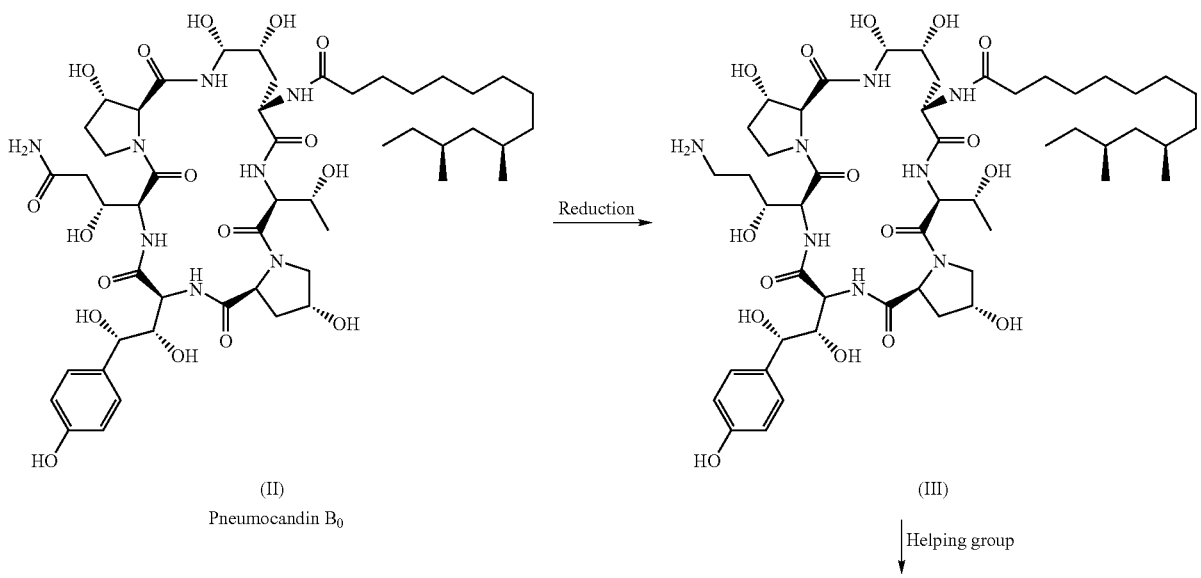

(II)
Pneumocandin $B_0$

Reduction (III)

Helping group

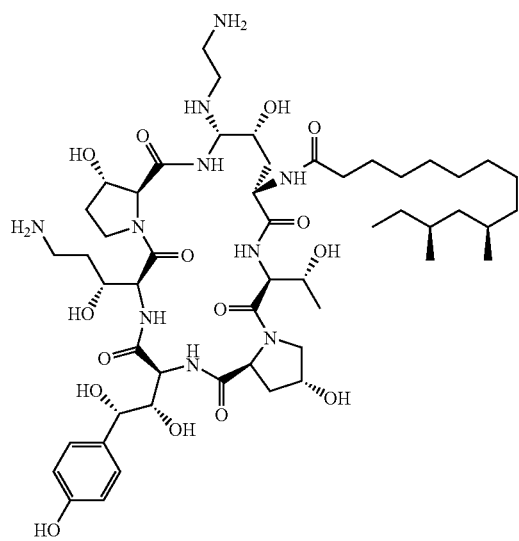

(I)
Caspofungin

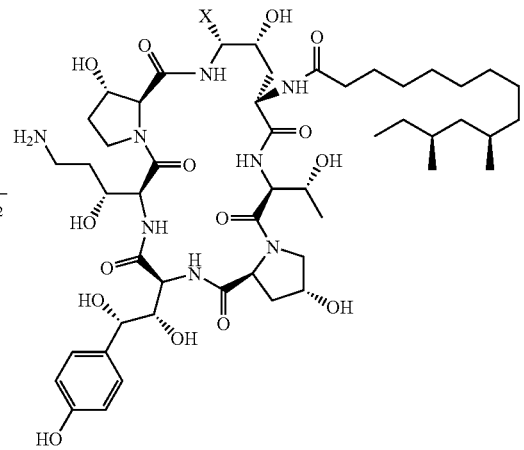

(IV)

When compound of formula IV is treated with 1,2-diaminoethane, caspofungin is released after substitution of the helping group X and removal of potential protecting groups.

The present invention therefore provides a compound of formula VII

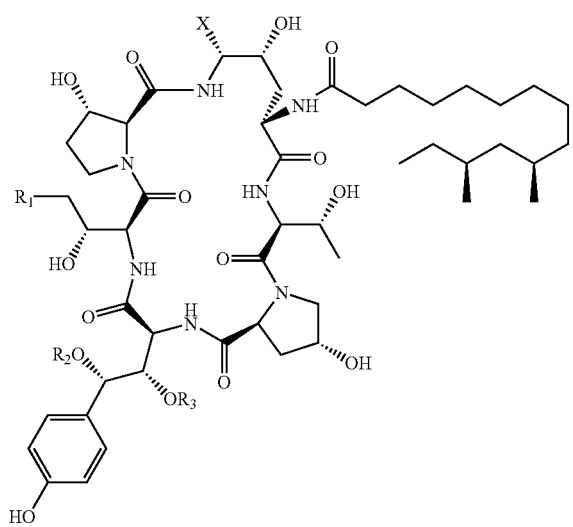

(VII)

or an acid addition salt or a solvate thereof, wherein $R_1$ is —(CO)NH$_2$, —CH$_2$NH$_2$ or —CN;
$R_2=R_3=$H or $R_2$ and $R_3$ together form a cyclic boronate or borate ester;
X is a helping group selected from the group consisting of i) a five or six membered heterocyclic aromatic ring and derivatives thereof comprising at least one N-atom being a part of an imine-group, wherein said N-atom forms the point of connection to the cyclohexapeptide ring, and ii) tetrazolyl and derivatives thereof for which a nitrogen atom forms the point of connection to the cyclohexapeptide ring.

The compounds of formula VII is particularly useful as intermediates in the synthesis of caspofungin and related compounds.

According to yet another aspect, intermediates being useful in the preparation of caspfungin and related compounds are provided having the formula

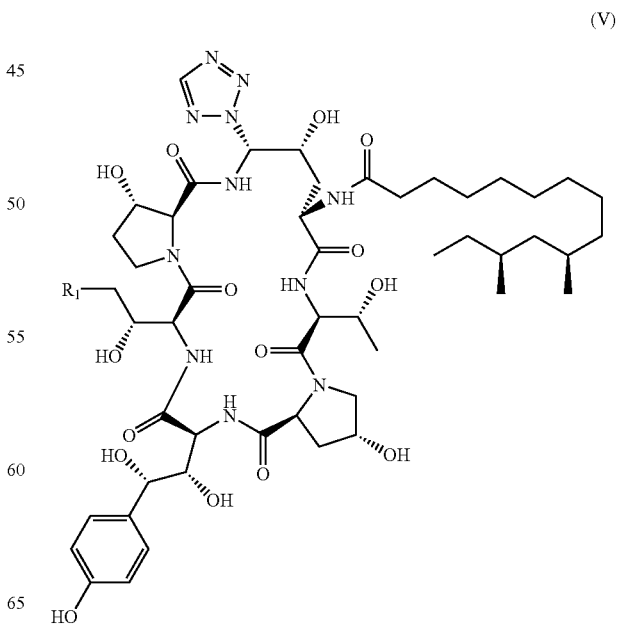

(V)

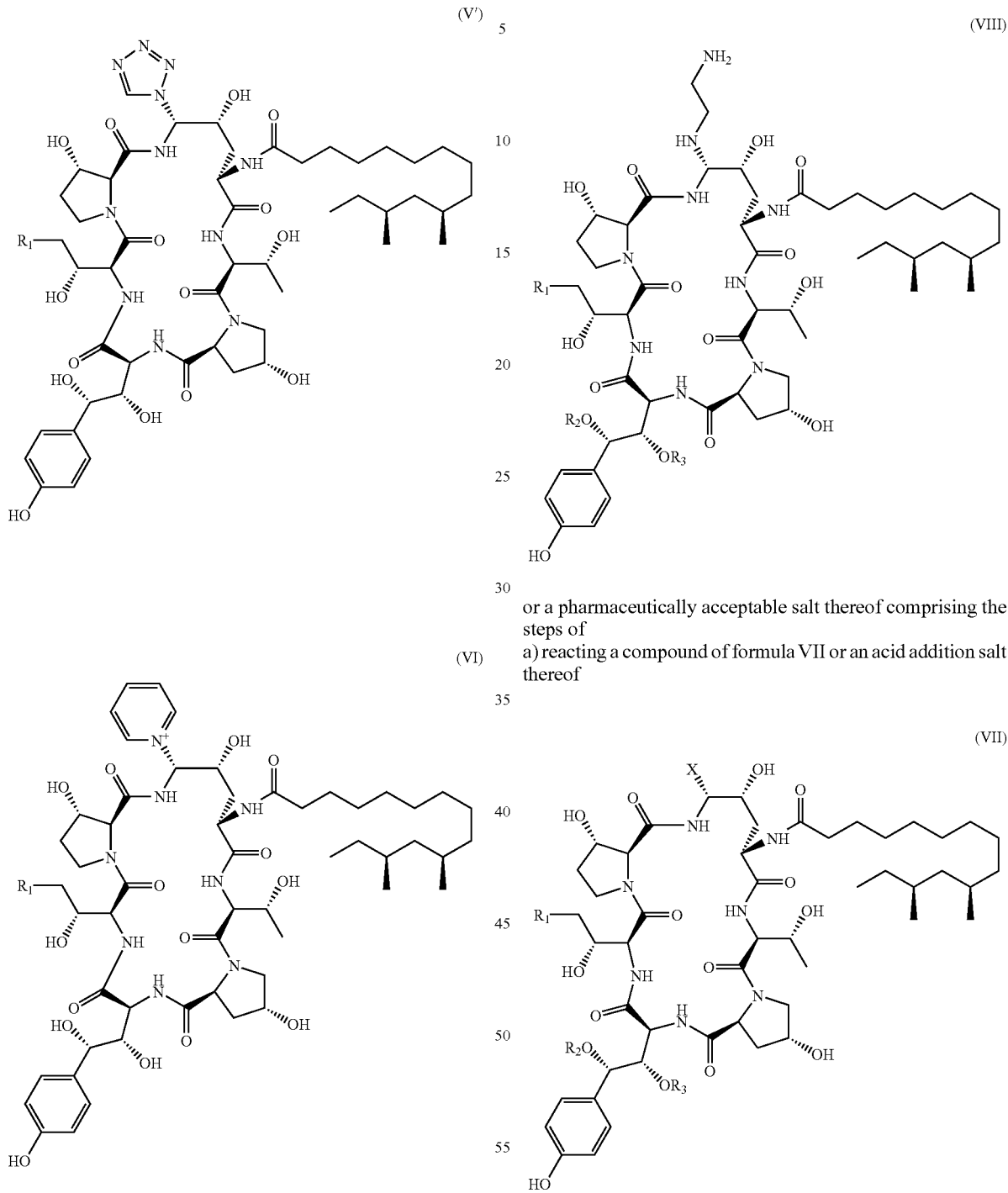

or an acid addition salt or a solvate thereof, wherein $R_1$ is —(CO)NH$_2$, —CH$_2$NH$_2$ or —CN. According to another aspect, a compound of formula (VII), (V), (V') and (VI), is provided wherein $R_1$ is —CH$_2$NH$_2$.

The present invention also provides a process for producing a compound of formula VIII or a pharmaceutically acceptable salt thereof comprising the steps of
a) reacting a compound of formula VII or an acid addition salt thereof wherein $R_1$ is —(CO)NH$_2$, —CH$_2$NH$_2$ or —CN;
$R_2$=$R_3$=H or $R_2$ and $R_3$ together form a cyclic boronate or borate ester;
X is a helping group selected from the group consisting of i) a five or six membered heterocyclic aromatic ring and derivatives thereof comprising at least one N-atom being a part of an imine-group, wherein said N-atom forms the point of connection to the cyclohexapeptide ring, and ii) tetrazolyl and derivatives thereof for which a nitrogen atom forms the point of connection to the cyclohexapeptide ring, with 1,2-diaminoethane to obtain a compound of formula VIII or a pharmaceutically acceptable salt thereof
and b) optionally isolating the compound of formula VIII or a pharmaceutically acceptable salt thereof as obtained in step a).

According to yet another aspect, a process for producing caspofungin (I) or a pharmaceutically acceptable salt thereof is provided, wherein said process comprises the steps of a) reacting the compound of formula IX or an acid addition salt thereof

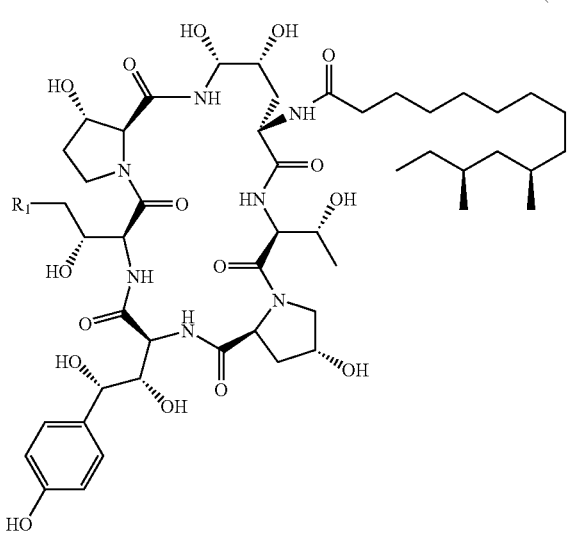

(IX)

wherein $R_1$ is —(CO)NH$_2$, —CH$_2$NH$_2$ or —CN with i) a five or six membered heterocyclic aromatic compound and derivatives thereof comprising at least one N-atom being a part of an imine-group, or ii) tetrazole and derivatives thereof to form a compound of formula VII

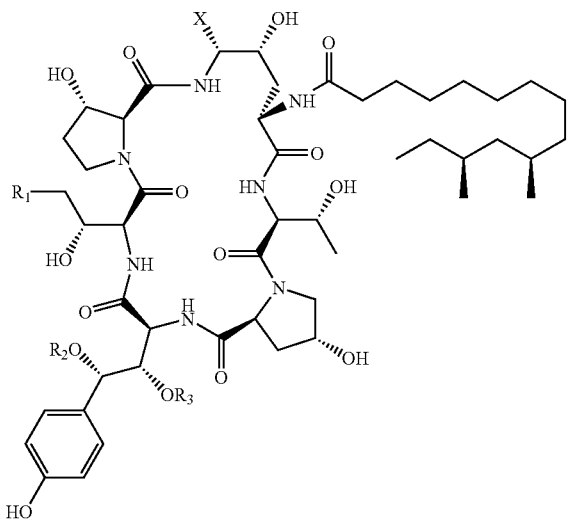

(VII)

wherein $R_1$ and X are as defined above;
$R_2 = R_3 = H$ or $R_2$ and $R_3$ together form a cyclic boronate or borate ester;

b) followed by substituting X with 1,2-diaminoethane to give a compound of formula VIII or a pharmaceutically acceptable salt thereof.

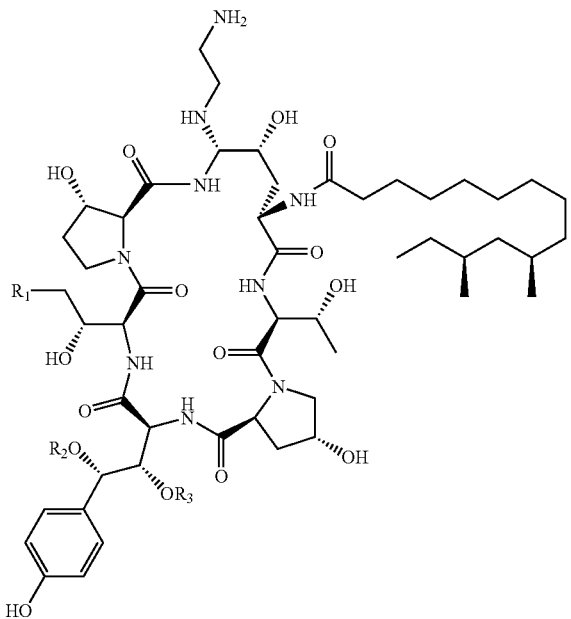

(VIII)

c) optionally isolating the compound of formula I or a pharmaceutically acceptable salt thereof, provided that if $R_1$ in formula IX is —(CO)NH$_2$ or —CN a reduction is performed before or after step a) or b), respectively to afford the compound of formula I as the final product.

According to another aspect, the process according to the present invention may be performed as a one-pot telescoped process wherein caspofungin is synthesised form pneumocandin $B_0$ without isolation of any intermediates.

According to one aspect of the process of the present invention, X is introduced in reaction with pyridine and the compound of formula VII is

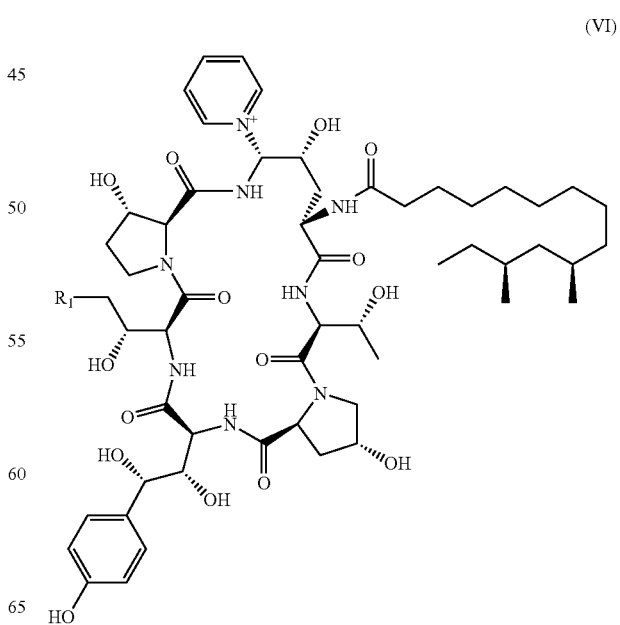

(VI)

or an acid addition salt or a solvate thereof.

According to yet another aspect of the process of the present invention, X is introduced in reaction with tetrazole and the compound of formula VII is (V)

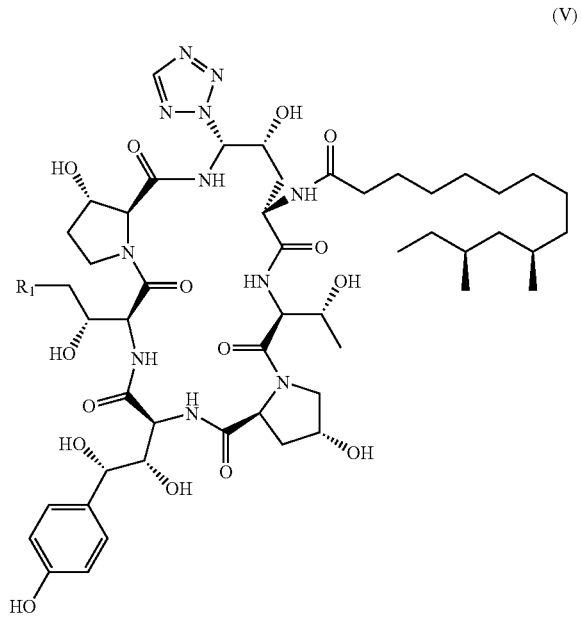

(V')

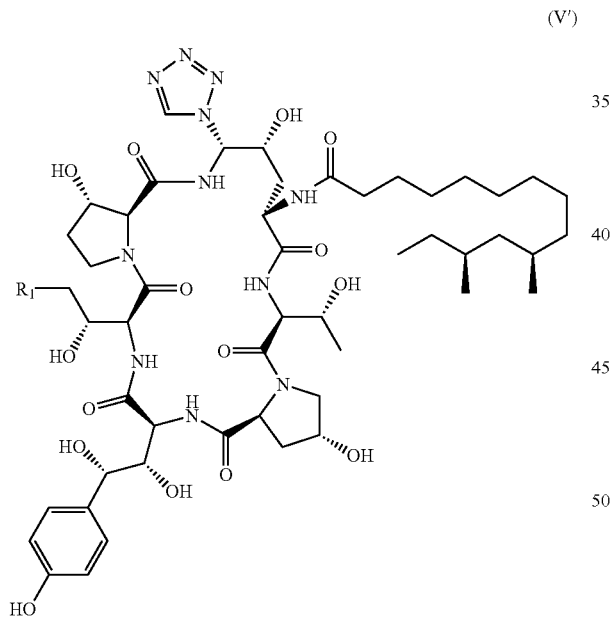

or an acid addition salt or a solvate thereof.

DETAILED DESCRIPTION OF THE INVENTION

The present invention will now be described in more detail with reference to figures and examples. The following description and examples intend to illustrate the present invention, and should in no way be considered limiting. Furthermore, the skilled person will acknowledge that various modifications may be introduced without departing from the scope of the invention. Accordingly, other embodiments of the present invention which are within the abilities of the skilled person are to be understood to be within the scope of the enclosed claims.

We have found that certain nitrogen nucleophiles may replace thiophenol as the helping group in the introduction of the caspofungin aminal side-chain. The term "helping group" denoted X in formula VII is selected from the group consisting of i) a five or six membered heterocyclic aromatic ring and derivatives thereof comprising at least one N-atom being a part of an imine group, wherein said N-atom forms the point of connection to the cyclohexapeptide ring, and ii) tetrazolyl and derivatives thereof for which a nitrogen atom forms the point of connection to the cyclohexapeptide ring.

The term "cyclohexapeptide ring" as used herein means the 21-membered macrocyclic ring constituting the peptide backbone of the compounds belonging to the echinocandin family, in particular caspofungin.

The use of a helping group X according to the present invention solves the problems of using thiophenol in the synthesis method for preparing caspofungin reported in the prior art.

Some nitrogen-containing aromatic heterocyclic compounds have been found efficient in the transformation of pneumocandin $B_0$ to caspofungin. Non-limiting examples of useful nitrogen nucleophiles for the introduction of helping groups are tetrazole and pyridine. Tetrazole may be substituted for the hemiaminal hydroxy function at −10° C. in the presence of an acid such as triflic acid, while pyridine requires elevated temperatures in the presence of e.g. triflic acid or pyridinium triflate. When tetrazole is substituted for the hemiaminal hydroxy function, the neutral compound V or V' is produced, while the cationic intermediate VI is formed when pyridine is introduced as the helping group, Scheme 2.

Scheme 2

(V)

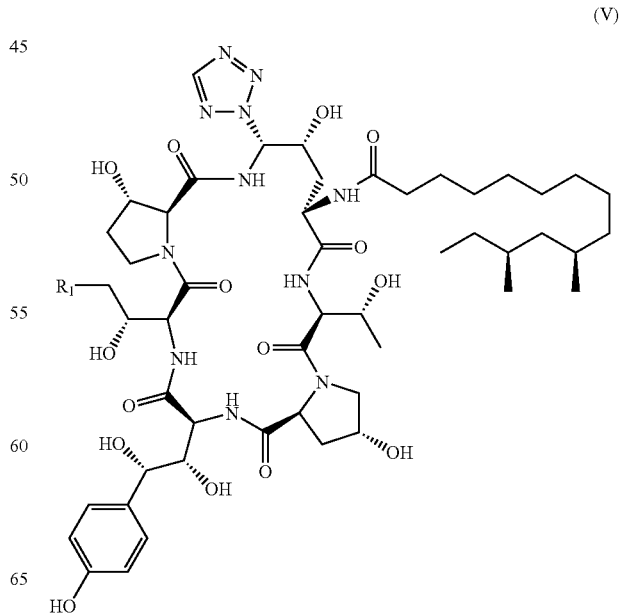

-continued

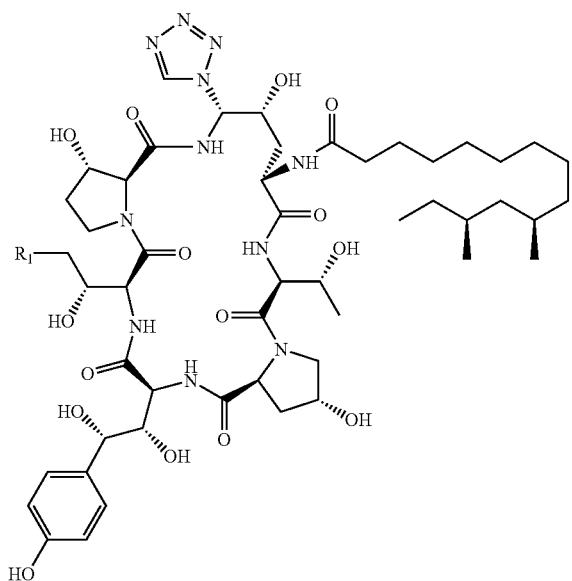

(V')

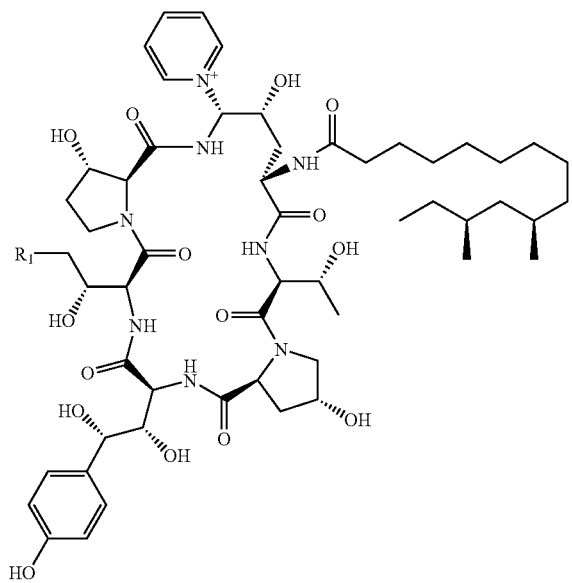

(VI)

The helping groups derived from tetrazole and pyridine are readily substituted with 1,2-diaminoethane with introduction of the caspofungin aminal side-chain, either directly in a telescoped process or as a separate step after isolation of the intermediate, yielding caspofungin.

It is to be understood that also other substituents than 1,2-diaminoethane may be substituted with X using the intermediates of formula VII according to the present invention. Non-limiting examples of other useful substituents may be found in e.g. WO 2007/057141 and U.S. Pat. No. 5,552,521.

Another advantage of the present invention is that the number of batch processes in the synthesis of caspofungin is reduced compared to the prior art. The method of the present invention is also suitable for a one-pot telescoped synthesis of caspofungin from pneumocandin $B_0$. A one-pot synthesis is in general favourable since it often results in improved efficiency and more economical operation of a chemical production plant. Lengthy separation processes and purification steps of intermediates are thus avoided. A one-pot synthesis is therefore also preferred due to the resulting saving of time, costs and equipment. Pneumocandin $B_0$ may thus according to the present invention be protected by reaction with phenylboronic acid, followed by reduction of the primary amide with borane in THF. After completion of the reaction, pyridine may be added and THF distilled off. Substitution of the hemiaminal hydroxy function with pyridine and introduction of the helping group may be effected when adding triflic acid, and finally, the target side-chain may be introduced by the addition of 1,2-diaminoethane to the reaction mixture. The preparation of caspofungin is thus fulfilled in a one-pot telescoped process according to the present invention.

Dependent on the work-up and the method of purification the product may be isolated as the free base or as an acid addition salt. Any pharmaceutical acceptable acid addition salt may be used according to the present invention. It is to be acknowledged that the skilled person based on the teaching of the present invention and his general knowledge is able to select a suitable pharmaceutical salt. In some of the examples listed below the double substitution sequence has been performed in the presence of triflic acid, and the reaction mixture is quenched with aqueous acetic acid. Variation of the conditions for chromatographic purification allow for the isolation of the product as either the acetic acid addition salt or the triflic acid salt, or as a mixture. A salt switch may also be carried out as a separate chemical operation.

EXAMPLES

The present invention will now be described in more detail with reference to examples, which are not to be contemplated as restrictive or limiting to the scope of the present invention and the enclosed claims.

HPLC analyses were performed with a Waters Symmetry C18 column, 250×4.6 mm, 100 Å, 5 μm; Column temperature: 45° C.; Mobile phase: Solution A: 0.1% v/v aqueous perchloric acid, Solution B: acetonitrile, gradient elution from 67/33 A:B to 35/65 A:B; Flow: 1.5 mL/min; Detection: 205 nm; Integrator setting: Peak area %; Solvent solution: acetonitrile/water 1:1. Mass spectra were obtained with electrospray ionisation, and the instrument was run in a positive mode. Analytes have been detected in the protonated form.

Example 1

Compound of Formula VIII, $R_1$=—(CO)$NH_2$, $R_1$=$R_2$=H

Pneumocandin $B_0$ (2.02 g, 1.90 mmol) and triflic acid (3.0 mL, 5.09 g, 33.9 mmol) were dissolved in pyridine (30 mL) at rt. The mixture was heated to 80° C. and stirred for 12 h in inert atmosphere. After cooling to 0° C., 1,2-diaminoethane (1.00 mL, 0.90 g, 15.0 mmol) was added, and the mixture was stirred over night. The reaction was quenched by adding the reaction mixture to a mixture of water (100 mL) and acetic acid (21 mL, 22.0 g, 0.37 mol), resulting in a solution with pH 5.0. The solution was loaded onto a 10 mm C18 chromatography column eluting with a gradient from 20% acetonitrile/80% water to 25% acetonitrile/75% water. Evaporation of the organic solvent and freeze drying of the rich cuts afforded 534 mg (22% yield) of the title compound as the triflic acid addition salt. Purity, HPLC: 87.8%.

$^1$H NMR (600 MHz, $CD_3OD$): δ 7.13 (2H, d, J 8.6 Hz), 6.74 (2H, d, J 8.6 Hz), 5.08 (1H, d, J 4.0 Hz), 5.02 (1H, d, J 3.5 Hz), 4.80 (1H, d, J 1.9 Hz), 4.56-4.52 (m), 4.37 (1H, dt, J 9.4, 3.9 Hz), 4.34 (1H, s), 4.31-4.25 (m), 4.21 (1H, d, J 3.8 Hz), 3.99-3.95 (m), 3.80-3.75 (m), 3.09 (1H, ddd, J 12.9, 6.5, 5.3 Hz), 2.98 (1H, ddd, J 13.0, 6.8, 5.3 Hz), 2.88 (1H, ddd, J 14.9, 6.7, 5.1 Hz), 2.81 (1H, ddd, J 13.4, 6.7, 5.2 Hz), 2.73 (1H, dd, J 15.4, 3.8 Hz), 2.46 (1H, dd, J 15.4, 9.5 Hz), 2.42 (1H, dd, J 13.4, 7.1 Hz), 2.26-2.18 (m), 2.10-2.03 (m), 1.97-1.90 (m), 1.63-1.52 (m), 1.51-1.46 (m), 1.45-1.39 (m), 1.38-1.20 (m), 1.14 (d, J 6.2 Hz), 1.12-1.03 (m), 0.91 (1H, dt, J 13.5, 7.0 Hz), 0.87 (3H, d, J 7.4 Hz), 0.85 (6H, d, J, 6.6 Hz); $^{13}$C NMR (150 MHz, CD$_3$OD): δ 177.0, 175.8, 173.94, 173.92, 173.4, 172.8, 172.6, 169.0, 158.5, 133.1, 129.7, 121.8 (q, $^1J_{C-F}$ 316 Hz), 116.2, 77.1, 75.8, 75.1, 71.3, 70.6, 70.3, 69.5, 68.1, 63.9, 62.6, 58.6, 57.2, 56.1, 55.3, 50.9, 47.1, 45.9, 43.1, 40.0, 39.7, 38.5, 38.1, 36.8, 36.4, 34.6, 32.9, 31.2, 31.1, 30.8, 30.6, 30.33, 30.32, 28.0, 27.0, 20.7, 20.2, 19.5, 11.6.

Example 2

Compound of Formula VIII, R$_1$=—(CO)NH$_2$, R$_2$=R$_3$=H

Pneumocandin B$_0$ (100 mg, 0.094 mmol) was dissolved in pyridine (2 mL), and triethylsilyl triflate (107 μL, 125 mg, 0.47 mmol) was added. The mixture was stirred at 80° C. while the reaction progress was monitored with HPLC. After stirring over night, HPLC indicated 72% conversion to a new compound (compound VI with R$_1$=—(CO)NH$_2$). LC-MS returned the mass m/z 1126.4 for the main product, confirming the pyridine substitution. The mixture was cooled to rt, and 1,2-diaminoethane (2 mL) was added. 15 min later HPLC demonstrated full conversion of the pyridine adduct to another new product for which LC-MS returned the mass m/z 1107.6 which is the expected mass for the title compound. The product was not isolated.

Example 3

Compound of Formula III

A mixture of pneumocandin B$_0$ (1.80 g, 1.69 mmol), phenylboronic acid (0.433 g, 3.55 mmol) and THF (20 mL) was stirred for 16 h at rt. The solvent was removed in vacuo, and the residual material was dissolved in THF (50 mL). This process was repeated twice, and then the powdered residue was dried at 50° C. in vacuum for 19 h. The powder was dissolved in anhydrous THF (75 mL), and N,O-bis(trimethylsilyl)trifluoroacetamide (BSTFA) (1.3 mL, 4.89 mmol) was added. The mixture was stirred at ambient temperature for 1 h, and cooled to 0° C. A solution of borane-THF complex (1.0 M in THF, 10 mL, 10 mmol) was added during 5 min, and the mixture was stirred at this temperature for 16 h. Aqueous hydrochloric acid (2.0 M, 9 mL, 18 mmol) was added, and the reaction mixture was stirred at 0° C. for 2 h. Water (100 mL) was added, and the product was isolated by chromatography on a 21 mm C18 column, using 26% acetonitrile/74% water as eluent, after washing the column with 15% acetonitrile/ 85% 0.014 M HCl after load. The rich cuts were pooled and freeze dried after removal of the organic solvent. Yield: 1.0 g (57%) of the title compound as the HCl salt. Purity, HPLC: 96.4%.

Example 4

Compound of Formula V or V'

A mixture of pneumocandin B$_0$ (1.07 g, 1.00 mmol), phenylboronic acid (0.244 g, 2.00 mmol) and 0.45 M tetrazole in acetonitrile (10 mL, 4.5 mmol) was cooled to −10° C. A solution of triflic acid (0.453 g, 3.00 mmol) in acetonitrile (1.5 mL) was added during 15 min. The clear reaction mixture was gently agitated at this temperature for 40 h and then diluted with acetonitrile (15 mL). A solution of sodium acetate trihydrate (0.408 g, 3.00 mmol) in water was added slowly, and the precipitate was collected by suction filtration and washed with cold acetonitrile (2×5 mL). Drying at reduced pressure afforded 1.07 g (96% yield) of the target compound as a white solid. Purity, HPLC: 69.3%. The tetrazole substitution was confirmed by LC-MS analysis which returned m/z 1117.59 for the main product.

Example 5

Caspofungin Triflic Acid Salt

Compound of formula III as the HCl-salt (100 mg, 0.095 mmol) prepared according to Example 3 was dissolved in pyridine (2 mL) at rt. Pyridinium triflate (640 mg, 2.86 mmol) was added, and the reaction mixture was heated to 80° C. and stirred for 8 h. The mixture was cooled to 0° C., and 1,2-diaminoethane (51 μL, 0.76 mmol) was added. When the reaction was complete (HPLC), water (15 mL) was added, and the solvents were removed in vacuo. Another portion of water (15 mL) was added, and the pH was adjusted to pH ~5. A small amount of methanol was added to keep the product dissolved. The solution was loaded onto a 10 mm C18 column, and the product was eluted using 25% acetonitrile/ 0.15% acetic acid as eluent. The rich cuts were pooled, and the organic solvent was removed. Freeze drying of the resulting aqueous solution afforded 41 mg (32% yield) caspofungin triflic acid addition salt. Purity, HPLC: 96.2%.
$^1$H NMR (600 MHz, CD$_3$OD): δ 7.11 (2H, d, J 8.5 Hz), 6.75 (2H, d, J 8.6 Hz), 4.99 (1H, d, J 3.3 Hz), 4.91 (1H, d, J 5.7 Hz), 4.69 (1H, d, J 2.1 Hz), 4.61-4.55 (m), 4.54 (1H, dd, J 11.6, 7.1 Hz), 4.49 (1H, dd, J 12.9, 4.3 Hz), 4.33-4.27 (m), 4.22 (1H, dd, J 8.0, 1.5 Hz), 4.17 (1H, d, J 4.9 Hz), 4.08-4.01 (m), 3.97 (1H, dd, J 11.1, 3.1 Hz), 3.84-3.76 (m), 3.08-3.05 (m), 3.01-2.95 (m), 2.94-2.88 (m), 2.84-2.77 (m), 2.43 (1H, dd, J 13.0, 6.8 Hz), 2.30-2.19 (m) 2.22-1.94 (m), 1.89-1.80 (m), 1.65-1.52 (m), 1.52-1.46 (m), 1.46-1.39 (m), 1.38-1.20 (m) 1.19-1.14 (m) 1.13-1.03 (m), 0.91 (1H, dt, J 13.8, 7.1 Hz), 0.87 (3H, d, J 7.4 Hz), 0.85 (6H, d, J 6.6 Hz); $^{13}$C NMR (150 MHz, CD$_3$OD): δ 176.4, 174.1, 173.7, 173.5, 172.72, 172.71, 168.8, 158.6, 133.0, 129.5, 121.8 (q, $^1J_{C-F}$ 316.5 Hz), 116.2, 77.4, 75.5, 75.1, 72.3, 71.3, 70.2, 69.3, 68.3, 64.3, 62.7, 58.3, 57.1, 56.1, 56.0, 51.2, 47.0, 45.9, 43.4, 40.3, 39.1, 38.5, 38.1, 36.9, 35.9, 34.6, 32.9, 31.2, 31.1, 30.8, 30.62, 30.57, 30.34, 30.31, 28.0, 27.1, 20.7, 20.2, 19.9, 11.6.

Example 6

Compound of Formula III

Phenylboronic acid (2.30 g, 18.9 mmol) was added to a suspension of pneumocandin B$_0$ (10.0 g, 9.39 mmol) in THF (500 mL). The mixture was heated at reflux temperature over night and dried by passing the refluxate through a soxhlet extractor containing molecular sieves (3 Å, 55 g). The temperature was lowered to 20° C., and BSTFA (5.0 mL, 18.8 mmol) was added. The mixture was stirred for 1 h at 20° C. and cooled to 0° C. Borane-THF complex (1.0 M in THF, 75.0 mL, 75.0 mmol) was added dropwise over 30 min, and the mixture was stirred at 0° C. for 19 h. Aqueous hydrochloric acid (2.0 M, 50 mL, 100 mmol) was added over 15 min, and the temperature was raised to 5° C. Water (550 mL) was added in one portion, and the mixture was stirred for 30 min. The product was isolated by chromatography on a 21 mm C18 column, eluted with 26% acetonitrile/water, following a wash with 20% acetonitrile/0.014M HCl. The rich cuts were pooled, and the organic solvent was removed. Freeze drying of the aqueous solution afforded 3.89 g (38% yield) of the title compound as the HCl salt. Purity, HPLC: 87.9%. LC-MS: main product m/z 1052.10, corresponding to [M+H$^+$].

Example 7

Caspofungin Acetic Acid Salt

A mixture of compound of formula III as the HCl-salt (10.0 g, 9.20 mmol) prepared according to Example 6, phenylboronic acid (2.48 g, 20.3 mmol), tetrazole in acetonitrile (0.45 M, 92 mL, 41.4 mmol) and THF (40 mL) was cooled to −10° C. A solution of triflic acid (4.14 g, 27.6 mmol) in acetonitrile (20 mL) was added to the reaction mixture at a rate of 0.5 mL/min. The mixture was stirred for 23 h, and methanol (75 mL) was added. 1,2-Diaminoethane (46 mL, 0.69 mol) was added dropwise over 30 min. The temperature was increased to 30° C., and the mixture was concentrated at reduced pressure to ca. 120 mL. The reaction mixture was stirred at 20° C. for 17 h. The mixture was quenched by simultaneous addition of the reaction mixture and acetic acid (64 mL, 1.12 mol) to a second reactor charged with acetic acid (20 mL, 0.35 mol) and water (600 mL) in addition rates suitable for maintaining the pH in the interval 3.8-5.2. The mixture was loaded onto a C18 column, and the column was washed with 10% acetonitrile/0.1M acetic acid, followed by 10% acetonitrile/0.15% acetic acid. The product was eluted with 22% acetonitrile/0.15% acetic acid. The rich cuts were pooled, and the organic solvent was removed. Freeze drying afforded 3.62 g (32% yield) of caspofungin as the acetic acid addition salt. Purity, HPLC: 97.9%. LC-MS: main product m/z 1094.09, corresponding to [M+H$^+$].

Example 8

Caspofungin, One-Pot Procedure

Pneumocandin B$_0$ (200 mg, 0.19 mmol) was suspended in THF (3.0 mL), and phenylboronic acid (23 mg, 0.19 mmol) was added. The reaction mixture was stirred at rt over night. Water was removed azeotropically by distillation of THF from the flask, addition of anhydrous THF, and continued distillation to dryness. The mixture was cooled to rt, and anhydrous THF (3.0 mL) was added, followed by BSTFA (15 μL, 0.56 mmol). The mixture was stirred for 1 h at rt and cooled to 0° C. Borane-DMS complex (0.11 ml, 1.13 mmol) was added slowly, and the mixture was stirred for 3 h. Additional borane-DMS complex (0.06 mL, 0.62 mmol) was added, and the reaction mixture was stirred for another 4 h. THF (5.0 mL) was added, and the mixture was stirred over night at 0° C. Pyridine (10 mL) and aqueous hydrochloric acid (2.0 M, 100 μL, 0.2 mmol) were added, and the mixture was concentrated at reduced pressure to about 3 mL. Triflic acid (0.3 mL, 3.38 mmol) was added, and the reaction mixture was stirred at 80° C. for 5 h. The mixture was cooled to 0° C., and 1,2-diaminoethane (0.40 mL, 6.0 mmol) was added. The mixture was then stirred over night at 0° C. HPLC spiking experiments with caspofungin verified the presence of the target compound in the reaction mixture. The purity of caspofungin in the reaction mixture was 18%.

Example 9

Crystallisation of Caspofungin Diacetate

A portion of the freeze-dried material as obtained in Example 7 (413 mg, 0.34 mmol) was dissolved in a mixture of ethanol (5.5 mL), water (0.52 mL) and acetic acid (26 μL, 0.46 mmol) at rt. Ethyl acetate was added dropwise until a stable suspension was formed, 6.5 mL. The mixture was stirred for 1 h, another portion of ethyl acetate (3.5 mL) was added, and the mixture was aged for another 1 h. The solid material was collected by suction filtration, dried on the filter for 30 min, and further dried at 30° C. in vacuo for 2 h. Yield: 236 mg (57%). LC-MS: main product m/z 1093.97, corresponding to [M+H$^+$].
$^1$H NMR (600 MHz, CD$_3$OD): δ 7.12 (2H, d, J 8.6 Hz), 6.74 (2H, d, J 8.6 Hz), 4.97 (1H, d, J 3.2 Hz), 4.92 (1H, d, J 5.8 Hz), 4.66 (1H, d, J 2.1 Hz), 4.60 (1H, dd, J 3.3, 6.2 Hz), 4.56-4.50 (m), 4.48 (1H, dd, J 4.4, 12.8 Hz), 4.33-4.27 (m), 4.22 (1H, dd, J 1.6, 8.0 Hz), 4.18 (1H, d, J 4.8 Hz), 4.08-4.04 (m), 4.03-3.99 (m), 3.98 (1H, dd, J 3.1, 11.1 Hz), 3.88-3.78 (m), 3.76 (1H, d, J 10.5 Hz), 3.05 (2H, t, J 7.1 Hz), 3.03-2.92 (m), 2.92-2.85 (m), 2.82-2.76 (m), 2.41 (1H, dd, J 6.7, 13.1 Hz), 2.30-2.18 (m), 2.11-2.01 (m), 2.01-1.92 (m), 1.90 (6H, s), 1.87-1.79 (m), 1.65-1.52 (m), 1.52-1.45 (m), 1.45-1.39 (m), 1.39-1.20 (m), 1.16 (3H, d, J 6.2 Hz), 1.13-1.01 (m), 0.95-0.89 (m), 0.89-0.83 (m); $^{13}$C NMR (150 MHz, CD$_3$OD); δ 180.1, 176.3, 174.2, 173.7, 173.5, 172.8 (2C), 168.9, 158.5, 133.0, 129.6, 116.2, 77.3, 75.6, 75.1, 72.1, 71.3, 70.1, 69.3, 68.2, 64.4, 62.8, 58.4, 57.2, 56.2, 56.0, 51.2, 47.1, 45.9, 43.9, 40.3, 39.0, 38.5, 38.1, 36.9, 35.7, 34.6, 32.9, 31.23, 31.16, 30.80, 30.78, 30.6, 30.4, 30.3, 28.0, 27.1, 24.2, 20.7, 20.2, 19.9, 11.6.

The invention claimed is:
1. Compounds of formula VII

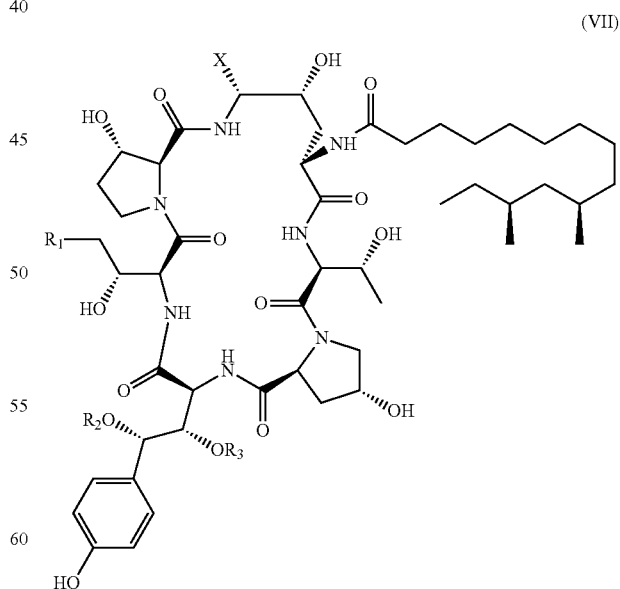

(VII)

or an acid addition salt thereof, wherein R$_1$ is —(CO)NH$_2$, —CH$_2$NH$_2$ or —CN;
R$_2$=R$_3$=H or R$_2$ and R$_3$ together form a cyclic boronate or borate ester;

X is a helping group selected from the group consisting of i) a five or six membered heterocyclic aromatic ring comprising at least one N-atom being a part of an imine-group, wherein said N-atom forms the point of connection to the cyclohexapeptide ring, and ii) tetrazolyl for which a nitrogen atom forms the point of connection to the cyclohexapeptide ring.

2. Compound according to claim 1, wherein $R_1$ is —CH$_2$NH$_2$.

3. Compound of the formula V or V'

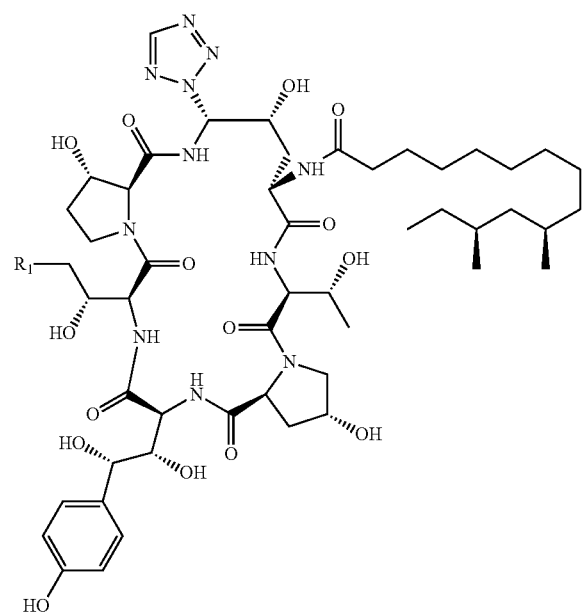

(V)

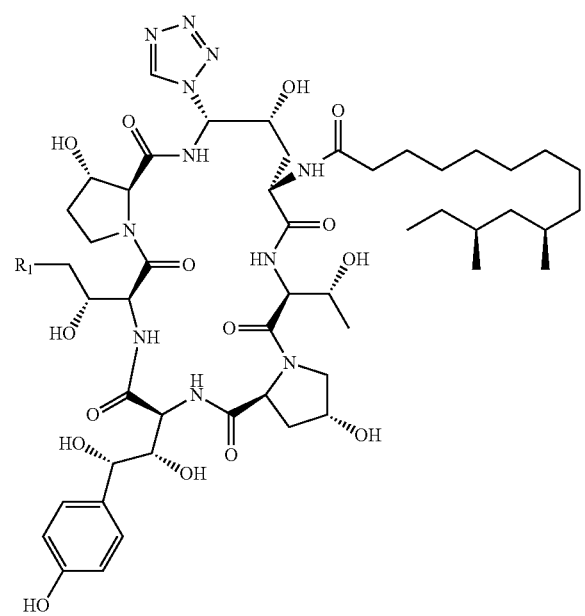

(V')

or an acid addition salt thereof, wherein $R_1$ is —(CO)NH$_2$, —CH$_2$NH$_2$ or —CN.

4. Compound according to claim 3 wherein $R_1$ is —CH$_2$NH$_2$.

5. Compound of the formula (VI)

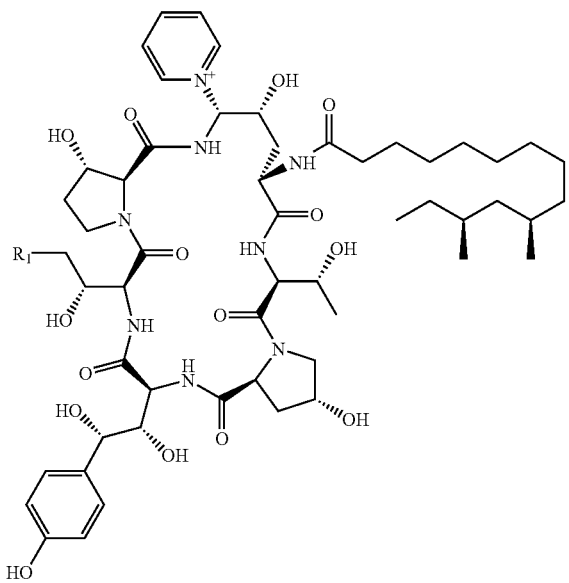

(VI)

or an acid addition salt thereof, wherein $R_1$ is —(CO)NH$_2$, —CH$_2$NH$_2$ or —CN.

6. Compound according to claim 5 wherein $R_1$ is —CH$_2$NH$_2$ or an acid addition salt thereof.

7. The process of producing a compound of formula VIII

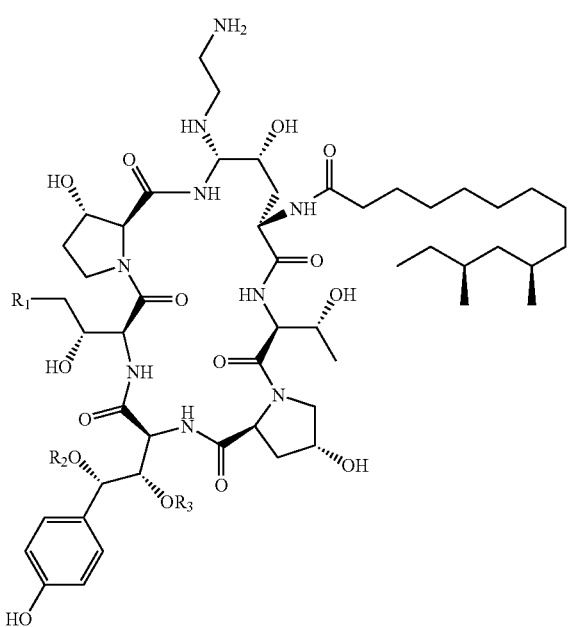

(VIII)

or a pharmaceutically acceptable salt thereof comprising the steps of a) reacting a compound of formula VII or an acid addition salt thereof

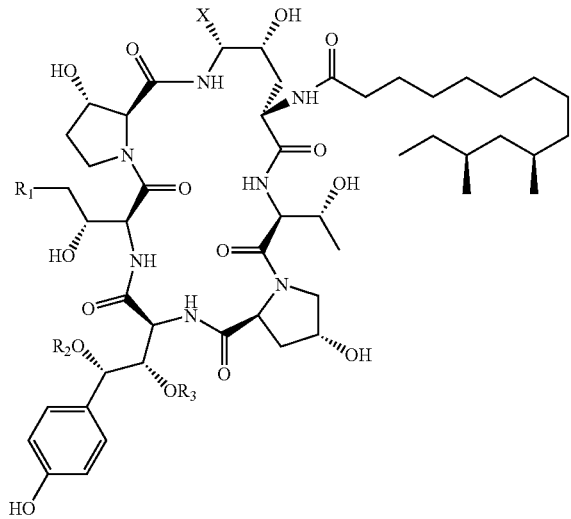

(VII)

wherein $R_1$ is —(CO)NH$_2$, —CH$_2$NH$_2$ or —CN;

$R_2=R_3=$H or $R_2$ and $R_3$ together form a cyclic boronate or borate ester;

X is a helping group selected from the group consisting of i) a five or six membered heterocyclic aromatic ring comprising at least one N-atom being a part of an imine-group, wherein said N-atom forms the point of connection to the cyclohexapeptide ring, and ii) tetrazolyl for which a nitrogen atom forms the point of connection to the cyclohexapeptide ring, with 1,2-diaminoethane to obtain a compound of formula VIII or a pharmaceutically acceptable salt thereof
and b) optionally isolating the compound of formula VIII or a pharmaceutically acceptable salt thereof as obtained in step a).

8. The process of producing caspofungin (I)

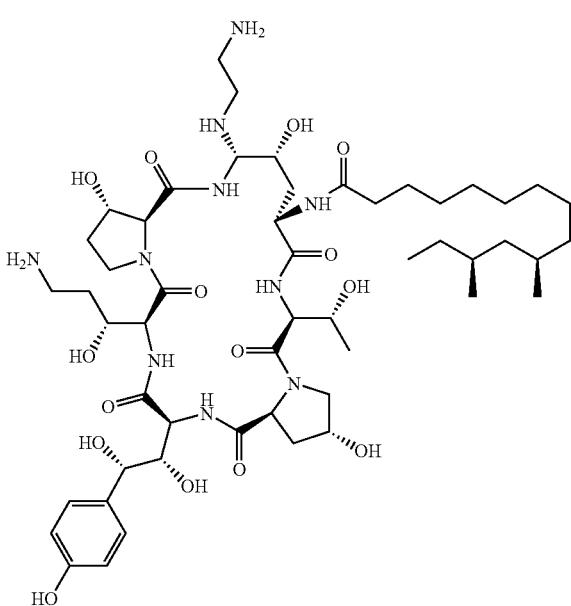

Caspofungin (I)

or a pharmaceutically acceptable salt thereof comprising the steps of a) reacting the compound of formula IX or an acid addition salt thereof

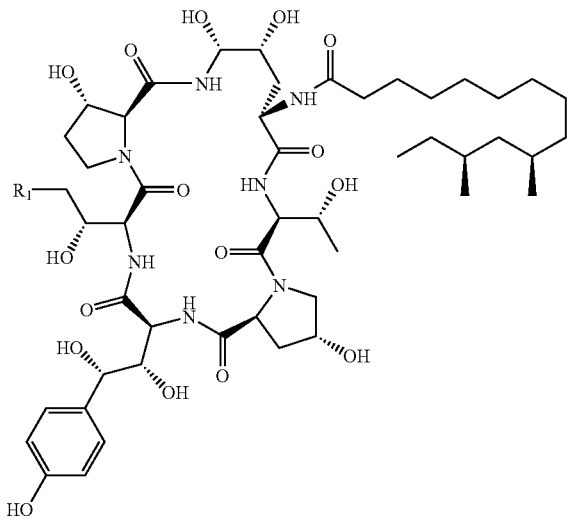

(IX)

wherein $R_1$ is —(CO)NH$_2$, —CH$_2$NH$_2$ or —CN with i) a five or six membered heterocyclic aromatic compound comprising at least one N-atom being a part of an imine-group, or ii) tetrazole to form a compound of formula VII

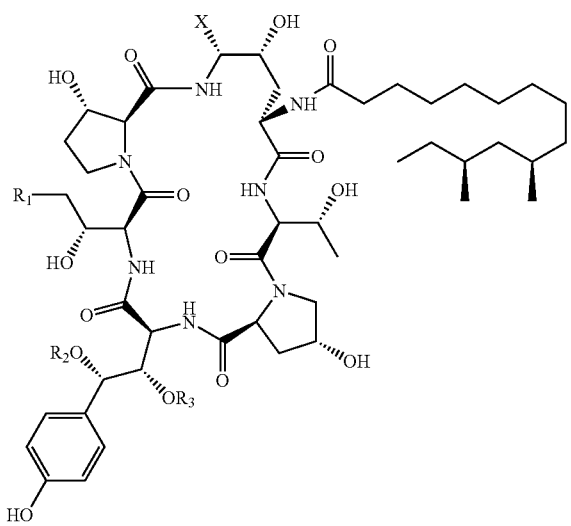

(VII)

wherein $R_1$ and X are as defined above;

$R_2=R_3=$H or $R_2$ and $R_3$ together form a cyclic boronate or borate ester;

b) followed by substituting X with 1,2-diaminoethane to give a compound of formula VIII or a pharmaceutically acceptable salt thereof (VIII)

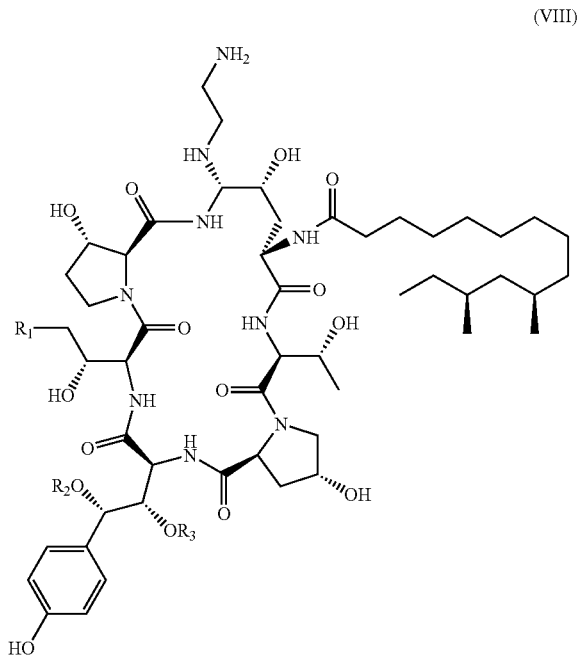

c) optionally isolating the compound of formula I or a pharmaceutically acceptable salt thereof, provided that if $R_1$ in formula IX is —(CO)$NH_2$ or —CN a reduction is performed before or after step a) or b), respectively to afford the compound of formula I as the final product.

9. A process according to claim 8 wherein step a) to c), including the reduction of $R_1$, are performed as a one-pot telescoped process.

10. A process according to claim 8 wherein X is introduced in reaction with pyridine and the compound of formula VII is (VI)

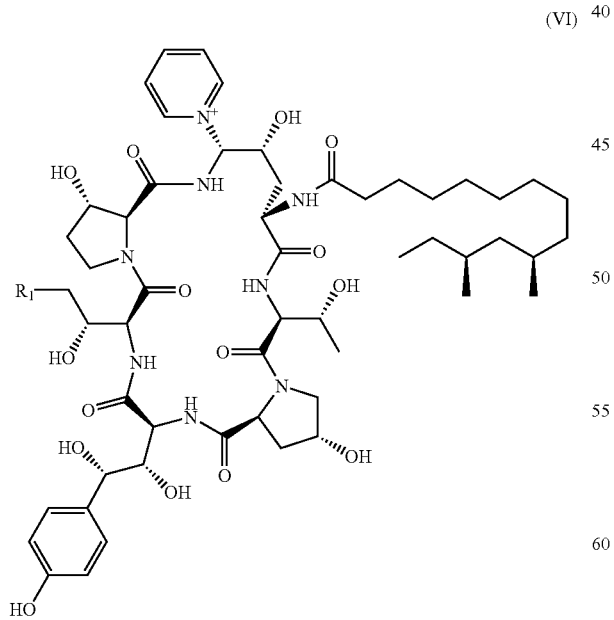

or an acid addition salt thereof.

11. A process according to claim 8 wherein X is introduced in reaction with tetrazole and the compound of formula VII is (V)

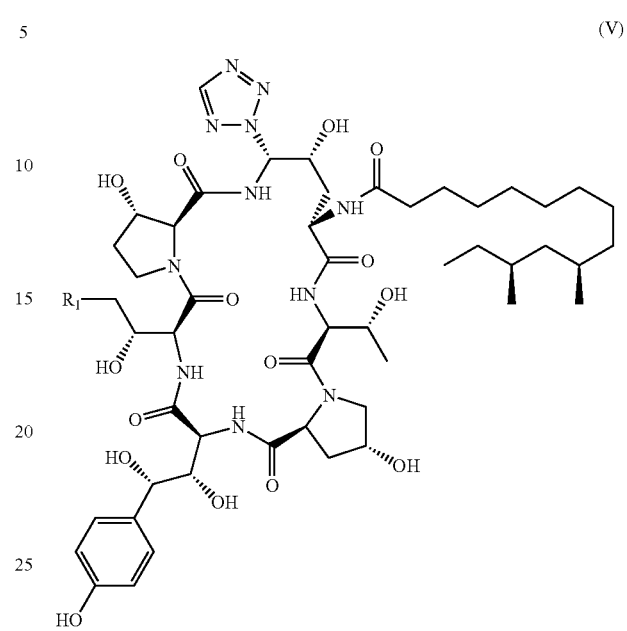

(V')

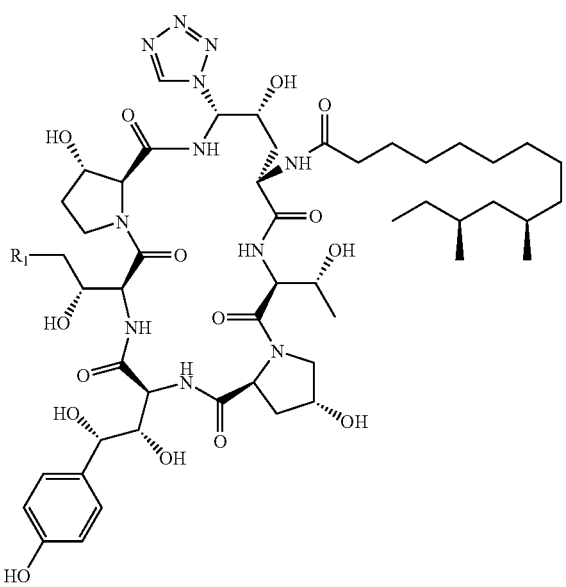

or an acid addition salt thereof.

* * * * *